United States Patent [19]

Milionis et al.

[11] 4,041,151

[45] Aug. 9, 1977

[54] RESIN COMPOSITIONS CONTAINING 0,0,0',0'-TETRAMETHYL 0,0'-THIODI-P-PHENYLENE PHOSPHOROTHIOATE

[75] Inventors: Jerry Peter Milionis, Somerset; Larry Dean Spicer, Princeton, both of N.J.

[73] Assignee: American Cyanamid Company, Stamford, Conn.

[21] Appl. No.: 592,433

[22] Filed: July 2, 1975

[51] Int. Cl.² ............... A61K 31/74; A01N 9/36
[52] U.S. Cl. ........................... 424/78; 424/33; 424/206
[58] Field of Search ............... 424/206, 14, 16, 31, 424/32, 78, 33

[56] References Cited

U.S. PATENT DOCUMENTS

| | | | |
|---|---|---|---|
| 3,318,769 | 5/1967 | Folckemer et al. | 424/219 |
| 3,852,416 | 12/1974 | Grubb et al. | 424/78 |

OTHER PUBLICATIONS

Whitlaw et al., J. Econ. Ent., vol. 61, No. 4, Aug. 1968, pp. 889-892.

*Primary Examiner*—V. D. Turner
*Attorney, Agent, or Firm*—H. G. Jackson

[57] ABSTRACT

This invention relates to novel resin compositions containing 0,0,0',0'-tetramethyl 0,0'-thiodi-p-phenylene phosphorothioate. More particularly, this invention relates to novel dry blended polyvinyl chloride resin compositions containing 0,0,0',0'-tetramethyl 0,0'-thiodi-p-phenylene phosphorothioate and to methods for preparing and using said resin compositions.

11 Claims, No Drawings

RESIN COMPOSITIONS CONTAINING 0,0,0',0'-TETRAMETHYL 0,0'-THIODI-P-PHENYLENE PHOSPHOROTHIOATE

BACKGROUND OF THE INVENTION 0,0,0',0'-Tetramethyl 0,0'-thiodi-p-phenylene phosphorothioate is disclosed in U.S. Pat. Nos. 3,317,636 and 3,459,856 issued May 2, 1967 and Aug. 5, 1969 respectively, as an insecticidal agent. This compound has been used by the armed forces in the form of powder and spray formulations for delousing humans and has been added to potable water in the form of discrete granules to control of mosquito larvae. In addition, it has been prepared as rubber pellets and plaster of paris cubes which were floated in water at breeding sites for mosquitoes. However, these latter preparations have not been especially effective for mosquito control.

Among the references which relate to the use of 0,0,0',0'-tetramethyl 0,0'-thiodi-p-phenylene phosphorothioate as an insecticidal agent are: (1) J. T. Whittaw, Jr., E. S. Evans, Jr. U.S. Army Environmental Hygiene Agency, Edgewood Arsenal, Md., J. of Economic Entomology, 61, 889–892 (1968); Entomological Special Study No. 31-006-71, Polymer Formulations of Durshan and Abate as mosquito larvicides (1970), U.S. Army Environmental Hygiene Agency, Edgewood Arsenal, Md.

2. R. T. Taylor, J. W. Miles, G. O. Guerrant and G. D. Books, controlled release formulations for use against aedes aegypti. Proceedings of the 56th Annual meeting of the N.J. Mosquito Extermination Association, Atlantic City, Mar. 19-21, 1969.

3. J. W. Miles and J. E. Woechst, "Formulations for Controlled Release of Abate in Water", *Pesticidal Formulations Research,* 1969, Advances in Chemistry No. 86, American Chemical Society, Washington, D.C.

While there have also been previous reports of 0,0,0',0'-tetramethyl 0,0'-thiodi-p-phenylene phosphorothioate incorporated into polyvinyl chloride (PVC), these formulations have differed from those of the subject invention in that such formulations included plasticizers and special plastisol type PVC resin and were used to form plastisols (emulsion resins).

The technique utilized in forming said plastisols requires that the liquid additives disperse the PVC resin at room temperature to form a viscous dispersion which is then fused at an elevated temperature. This plastisol technique requires that a specified plastisol type polyvinyl resin be used, and the fusion occurs at an elevated temperature either after the solution has been poured into a mold or after a hot mold has been dipped into the solution. After fusion the plastisols were evaluated for mosquito control. However, in these tests it is indicated that the plastisols did not release sufficient phosphorothioate compound into the aqueous breeding site of the mosquito larvae to achieve mosquito control.

SUMMARY OF THE INVENTION

This invention relates to novel dry blended extrudable and extruded polyvinyl chloride resin compositions containing, as the essential active ingredient, a pesticidally effective amount of 0,0,0',0'-tetramethyl 0,0'-thiodi-p-phenylene phosphorothioate and characterized by extended residual pesticidal activity and low mammalian toxicity.

The compositions of the invention are generally prepared in the finished form of extruded flexible sheets, strips, swatches or the like, and are particularly well suited to use in the manufacture of pesticide, especially siphonapteracide, collars for pet companion animals, particularly dogs and cats, and farm animals.

The polyvinyl chloride resins which may be utilized in the preparation of compositions of this invention are solids at room temperature. They have a weight average molecular weight of from 60,000 to 280,000 and an inherent viscosity of from about 0.5 to 1.2 determined by the A.S.T.M. Method D-1243-58T — Method A. In this method inherent viscosity is determined on a solution of 0.2 g. of resin in 100 ml. of cyclohexanone at 30° C.

The resins which may be employed in the manufacture of the compositions of this invention are polyvinyl chloride resins characterized by the above-indicated molecular weight and viscosity measurements.

In accordance with this invention, it has been found that resin compositions comprising a polyvinyl chloride resin having a weight average molecular weight of from 60,000 to 280,000 and preferably 80,000 to 230,000 and an inherent viscosity between about 0.5 and 1.2 and preferably between 0.67 and 1.07 and from about 13 to 50% by weight and preferably 18% to 50% by weight of 0,0,0',0'-tetramethyl 0,0-thiodi-p-phenylene phosphorothioate, are highly effective for the control of insect pests, particularly siphonaptera, (fleas) such as (*Ctenocephalides canis*) and (*Ctenocephalides felis*) which infest companion and farm animals.

Surprisingly, we have found that 0,0,0',0'-tetramethyl 0,0'-thiodi-p-phenylene phosphorothioate is not only a superior pesticide, but also an excellent plasticizing agent and may be used exclusively as both the pesticidal agent and the plasticizing agent in the manufacture of the preferred extruded and extrudable compositions of this invention. Preferred compositions comprise from 36% to 50% by weight of 0,0,0',0'-tetramethyl 0,0'-thiodi-p-phenylene phosphorothioate, from about 45% to about 63% by weight of the polyvinyl chloride resin having a weight average molecular weight of from 60,000 to 280,000 and preferably 80,000 to 230,000 and an inherent viscosity of from about 0.5 to 1.2 and preferably 0.67 to 1.07, from 1% to 3% by weight of a heat stabilizing agent for the resin and from about 0.0% to 2.0% by weight of a lubricant. These preferred compositions are preferably free of additional and/or secondary plasticizing and pesticidal agents; however, said preferred compositions may contain a small amount, for example 0.1% to 2.0% by weight of an organic or inorganic pigment. Where pigments are employed the percentage of resin in the compositions can be adjusted to compensate for the added pigment.

Other preferred extrudable compositions of this invention contain from about 13% to 40% and preferably 18% to 40% by weight of 0,0,0',0'-tetramethyl 0,0'-thiodi-p-phenylene phsophorothioate, from 22.5% to 7.6% by weight of a plasticizing agent having a molecular weight of from 400 to 1000 and preferably selected from the group consisting of epoxidized soybean oil, octyl epoxytallate (Flexol E.P.-8, product of Union Carbide Co.), epoxidized linseed oil, epoxidized tall oil ester and epoxidized butyl ester of linseed oil acids, from 1% to 3% by weight of a heat stabilizing agent for the resin, from 0.0% to 2.0% by weight of a lubricant and from 47.4% to 63.5% and preferably 47.4% to 58.5% by weight of a polyvinyl chloride resin having a weight average molecular weight of from 60,000 to 280,000 and preferably 80,000 to 230,000 and an inherent viscosity of about 0.5 to 1.2 and preferably 0.67 to 1.07 determined by A.S.T.M. Method D-1243-58T-Method A. These compositions may also contain from 0.1% to 2.0% by weight of an organic or inorganic pigment. As with the other preferred compositions, addition of pigment is compensated for by adjusting the resin content accordingly.

Still other preferred compositions of this invention contain 32% to 40% by weight of 0,0,0',0'-tetramethyl 0,0'-thiodi-p-phenylene phosphorothioate, from 6.5% to 2.75% by weight of dioctylphthalate, such as di-n-octylphthalate or di-(2-ethylhexyl)phthalate, from 1% to 3% by weight of a heat stabilizing agent for the resin, from 0.0% to 2.0% by weight of a lubricant, and from 52.25 to 60.5% by weight of a polyvinyl chloride resin having a weight average molecular weight of from 60,000 to 280,000 and preferably 80,000 to 230,000 and an inherent viscosity of from about 0.5 to 1.2 and preferably 0.67 to 1.07 as determined by A.S.T.M. Method D-1243-58T Method A. From about 0.1% to 0.5% by weight of a pigment, either organic or inorganic, may also be added with appropriate compensation of the resin concentration.

Among the heat stabilizing agents which may be employed in the compositions of the present invention are the organo metal stabilizers conventionally used in the preparation of extrudable polyvinyl chloride resins. These include organotin stabilizers; organo barium, cadmium, and lead stabilizers; zinc and calcium salts and mixtures or organo barium and cadmium stabilizers.

Exemplary of the lubricants which may be used in the compositions of this invention are calcium stearate, stearic acid, paraffin waxes, magnesium stearate, aluminum stearate, amide waxes, low molecular weight polyethylene and where a lead stabilizer is used, lead stearate.

Pigments which may be added to the extrudable compositions of this invention include inorganic pigments such as carbon black and titanium dioxide and organic pigments such as quinacridones, anthraquinones, litholrubine and alizarine maroon.

Exemplary of the polyvinyl chloride resins which can be used in the preparation of the resin compositions of this invention are the Diamond Alkali Company's polyvinyl chloride resins, CR80A, FCR, PVC 30, PVC 33, PVC 35, PVC 40, PVC 7-44 and characterized as follows:

| Resins | Inherent Viscosity ASTM D-1243-58T (A) | Approximate Weight Average Molecular Weight |
|---|---|---|
| Diamond FCR | 0.55 | 60,000 |
| Diamond PVC 30 | 0.57 | 60,000 |
| Diamond PVC 35 | 0.70 | 85,000 |
| Diamond PVC 40 | 0.80 | 120,000 |
| Hooker Rucon B-34 | 1.07 | 230,000 |
| Hooker Rucon B-38 | 1.19 | 280,000 |

The dry blended extrudable compositions of this invention are converted into extruded sheets, strips, ribbons or the like by dry blending the finely divided, solid, low molecular weight polyvinyl chloride resin with the vinyl stabilizer and the lubricant and incorporating into the blended material the desired amount of 0,0,0',0'-tetramethyl-0,0'-thiodi-p-phenylene phosphorothioate as the pesticidal agent and plasticizing agent. Additional plasticizing agent, selected from those mentioned above, may be added to prepare the desired extruded composition and where desired, pigment or dye may be incorporated in the blend. When the mixture is thoroughly dry blended it is charged to an extruder, and extruded at a stock temperature of about 160° C at exit. In operation we have found it most desirable to operate at a relatively low temperature in order to avoid thermal degradation of the phosphorothioate pesticidal and plasticizing agent. Preferred stock extrusion temperature is preferably between about 150° C and 180° C.

The extrudate from this process is obtained in the form of a flexible plastic strip or sheet which is readily fashioned into collars for pet companion animals or farm animals. Extruded strips simply require the addition of a buckle or other fastening means to complete the collar. Sheets may, of course, be cut into strips to which a buckling device may be appended and a collar prepared; or they may be cut into strips and coated on one side with adhesive such that the strips can be secured to the inside of a conventional animal collar.

Unlike many of the pest control collars and devices presently available which rely on the high vapor pressure of the pesticide to achieve pest control by funigant action, the phosphorothioate of the present compositions has a very low vapor pressure and achieves control of insect pests, especially fleas, by topical action.

Advantageously, the compositions of this invention have a very low mammalian toxicity. They have not been found to cause dermatitis on cats, dogs or the like, when used in contact with the animals coat for an extended period of 9 months or more. Moreover, they have been found to be completely effective for the control of fleas on cats and dogs for this period and do not show signs of diminishing activity even at this extended period.

SPECIFIC EXAMPLES

The advantages of this invention are further demonstrated by the following examples.

EXAMPLE 1

Preparation of PVC-0,0,0',0'-Tetramethyl 0,0'-thiodi-p-phenylene phosphorothioate Extrudable Resin Composition One thousand grams of Diamond 40 PVC resin, inherent viscosity 0.80 determined by A.S.T.M. D1243-58T (Method A), weight average molecular weight 120,000 (number average molecular weight 50,000), is charged to a Prodexhenschel mixer along with 5 g. stearic acid, 2 g. of carbon black and 20 g. of Thermolite 831-di-n-octyltin maleate polymer PVC heat stabilizing agent. The mixer is run at high speed (3600 rpm) until the temperature of the mixture is 175° F, 930 g. of 0,0,0',0'-tetramethyl 0,0'-thiodi-p-phenylene phosphorothioate (90% potency) is then added and mixing is continued.

When addition of the phosphorothioate is complete and the temperature of the mixture reaches 200° F, the speed of mixing is reduced to 1800 rpm and the batch discharged. The hot dry blend is then cooled and ready for extrusion.

The extrusion composition is then charged to the feed hopper of the extruder and extruded through a horizontal ribbon die having a ⅜ inch wide slot ⅛ inch thick.

Extrusion is accomplished with the mixture heated from 250° F at the rear feed to 330° F at the die zone and an extruded stock temperature of 163° C (326° F). This extrusion is conducted with a head pressure of 300 psi. Circulating water is used to cool the feed throat under the feed hopper as well as the extrudate exiting the die.

The extruded strip is then cut into 2 foot lengths to which a buckle is attached.

The animal collars thus prepared are free of secondary plasticizing and insecticidal agents other than the above-mentioned phosphorothioate which amounts to 47.5% (42.8% real) by weight of the composition.

The above procedure is repeated using 1000 g. of the above-identified PVC resin (inherent viscosity 0.80), 20 g. of di-n-octyltin, maleate polymer, 750 or 800 g. of the above said phosphorothioate, 0 or 2 g. of carbon black, and either 50 g. of dioctyl phthalate or 150 g. of epoxidized soybean oil.

The above compositions, all of which provide highly effective, easy to process, siphonapteracidal animal collars, are reported in parts by weight of composition and % w/w technical and real for the phosphorothioate.

Table I

| Siphonapteracidal Compositions | | | | |
|---|---|---|---|---|
| Compound | Parts by Weight | | | |
| Polyvinyl chloride (Inherent Viscosity 0.80) | 100 | 100 | 100 | 100 |
| Di-n-Octyltin maleate polymer | 2 | 2 | 2 | 2 |
| Stearic acid | 0.5 | 0.5 | 0.5 | 0.5 |
| 0,0,0',0'-Tetramethyl 0,0'-thiodi-p-phenylene phosphorothioate (Technical 90% potency) | 93 | 80 | 80 | 75 |
| Di (2-ethylhexyl) phthalate | — | — | — | 5 |
| Octylepoxytallate | — | 15 | 15 | — |
| Carbon black | 0.2 | 0.2 | — | 0.2 |
| % 0,0,0',0'-Tetramethyl 0,0'-thiodi-p-phenylene phosphorothioate | 47.5* | 40* | 40* | 40* |
|  | 42.8** | 36** | 36** | 36** |
| % Plasticizer (secondary) | 0 | 7.6 | 7.6 | 2.75 |

\* = % Technical
\*\* = % Real

EXAMPLE 2

Effective levels of 0,0,0',0'-Tetramethyl 0,0'-thiodi-p-phenylene phosphorothioate as a Plasticizing Agent for Polyvinyl Chloride Resin Following the procedure of Example 1, resin compositions are prepared which are free of any secondary plasticizing agent. Materials used are reported as parts by weight. Data obtained are reported in Table II below. In the preparations reported the above-mentioned phosphorothioate is technical material 90% potency.

Table II

| Plasticizing Effect of 0,0,0',0'-Tetramethyl 0,0'-thiodi-p-phenylene phosphorothioate on Polyvinyl Chloride Resin | | | | | | |
|---|---|---|---|---|---|---|
| Compound | Parts by Weight | | | | | |
| Polyvinyl Chloride (Inherent Viscosity 0.80) | 100 | 100 | 100 | 100 | 100 | 100 |
| Di-n-Octyltin maleate polymer | 2 | 2 | 2 | 2 | 2 | 2 |
| Stearic acid | 0.5 | 0.5 | 0.5 | 0.5 | 0.5 | 0.5 |
| 0,0,0',0'-Tetramethyl 0,0'-thiodi-p-phenylene phorothioate (Technical 90% potency) | 10 | 20 | 70 | 100 | 120 | 150 |
| 0,0,0',0'-Tetramethyl 0,0' thiodi-p-phenylene phosphorothioate | 8*  7.2** | 16.3*  14.7** | 40.6*  36.5** | 49.4*  44.5** | 53.9*  48.5** | 59.4*  53.5** |
| Comments | Hard to process | Very hard and very brittle | Easy to process | Easy to process flexible | Easy to process very flexible | Hard to process soupy |

\* = % Technical
\*\* = % Real

EXAMPLE 3

Effective of Secondary Plasticizing Agents on PVC - 0,0,0',0'-Tetramethyl 0,0'-thiodi-p-phenylene phosphorothioate Extrudable Resin Compositions Following the procedure of Example 1, resin compositions containing polyvinyl chloride resin, 0,0,0',0'-tetramethyl 0,0'-thiodi-p-phenylene phosphorothioate as the primary plasticizing agent and the siphonapteracidal agent and a secondary plasticizing agent, are prepared to determine the effect of said secondary plasticizing agent on the composition. Compositions and physical observations relating thereto are reported in Table III below, where it can be seen that compositions containing 18% to 40% by weight of the above-said phosphorothioate and 22.5% to 7.6% of a plasticizing agent having a molecular weight of 400 to 1000 and selected from epoxidized oils such as soybean oil, linseed oil, tall oil ester and butyl ester of linseed oil acids are extrudable compositions, useful as siphonapteracidal animal collars.

These data also demonstrate that compositions containing 32% to 40% by weight of the above-named phosphorothioate and from 6.5% to 2.75% of dioctylphthalate, are also extrudable compositions useful in the manufacture of siphonapteacidal animal collars.

Table III

| Effective of 0,0,0',0'-Tetramethyl 0,0'-thiodi-p-phenylene phosphorothioate With and Without Secondary Plasticizers On Flexibility of Extruded PVC Resin Compositions | | | | | |
|---|---|---|---|---|---|
| Compound | Parts by Weight | | | | |
| Polyvinyl Chloride Resin (Inherent Viscosity 0.80) | 100 | 100 | 100 | 100 | 100 |

Table III-continued

Effective of 0,0,0',0'-Tetramethyl 0,0'-thiodi-p-phenylene phosphorothioate With and Without Secondary Plasticizers On Flexibility of Extruded PVC Resin Compositions

| Compound | Parts by Weight | | | | |
|---|---|---|---|---|---|
| Di-n-Octyltin Maleate Polymer | 2 | 2 | 2 | 2 | 2 |
| Stearic Acid | 0.5 | 0.5 | 0.5 | 0.5 | 0.5 |
| 0,0,0',0'-Tetramethyl 0,0'-thiodi-p-phenylene phosphorothioate (Technical) | 75 | 51.75 | 49.0 | 49 | 29.5 |
| Di (2-ethylhexyl) phthlate | 5 | 17.25 | 11.5 | 10.5 | 15.1 |
| Carbon Black | — | — | — | — | — |
| Octylepoxytallate | — | — | — | — | — |
| Above-mentioned Phosphorothioate | | | | | |
| % Technical | 40 | 30 | 30 | 30 | 20 |
| % Real | 36 | 27 | 27 | 27 | 18 |
| % Plasticizer | 2.75 | 10 | 7.1 | 6.5 | 10.3 |
| Comments | Flexible | Overly Flexible | Overly Flexible | Flexible | Too Stiff |
| Polyvinyl Chloride Resin (Inherent Viscosity 0.80) | 100 | 100 | 100 | 100 | 100 | 100 |
| Di-n-Octyltin Maleate Polymer | 2 | 2 | 2 | 2 | 2 | 2 |
| Stearic Acid | 0.5 | 0.5 | 0.5 | 0.5 | 0.5 | 0.5 |
| 0,0,0',0'-Tetramethyl 0,0'-thiodi-p-phenylene phosphorothioate (Technical) | 93 | 35 | 80 | 93 | 75 | 45 |
| Di (2-ethylhexyl) Phthalate | — | — | — | — | — | — |
| Carbon Black | — | — | 0.2 | 0.2 | 0.2 | 0.2 |
| Octylepoxytallate | — | 40 | 15 | — | — | 35 |
| Above-mentioned phosphorothioate | | | | | | |
| % Technical | 47.5 | 20 | 40 | 47.5 | 40 | 24.63 |
| % Real | 42.8 | 18 | 36 | 42.8 | 36 | 22.2 |
| % Plasticizer | 0 | 22.54 | 7.6 | 0 | 2.75 | 19.16 |
| Comments | Flexible | Flexible | Flexible | Flexible | Flexible | Flexible |

EXAMPLE 4

0,0,0',0'-Tetramethyl 0,0'-thiodi-p-phenylene phosphorothioate Flea Collar Activity Against Ctenocephalides Felis on Dogs Twelve groups of three to four dogs each are infested with 100 adult *Ctenocephalides felis* 3 days prior to placing a flea collar around the neck of each dog. Each dog is systematically examined daily for fleas presence or absence. Complete flea control observed within 1 week from the time the collar is placed on the dog is considered effective control. Each dog is reinfested weekly with 100 adult *C. felis* and examined daily thereafter for fleas. Effective control is considered complete control of *C. felis* on all dogs within 1 week of reinfestation.

All dogs are fed Purina High Protein Dog meal once daily and all are provided water ad libitum. The dogs are housed in individual cages with grate bottom floors.

Compositions of extruded collars tested are reported in Table IV below in parts by weight and % w/w of the phosphorothioate.

Observations are reported in Table V.

From the data in Table V it can be seen that collars, 1,2,4,7,8,9,10 and 11 are highly effective for the control of fleas on dogs for an extended period up to 30 weeks or more.

Table IV

| Flea Collar Compositions | | | | | | | | | | | |
|---|---|---|---|---|---|---|---|---|---|---|---|
| Compound | Parts by Weight | | | | | | | | | | |
| Collar Number | 1 | 2 | 3 | 4 | 5 | 6 | 7 | 8 | 9 | 10 | 11 |
| Polyvinyl Chloride Resin (Inherent Viscosity 0.80) | 100 | 100 | 100 | 100 | 100 | 100 | 100 | 100 | 100 | 100 | 100 |
| Di-n-Octyltin Maleate Polymer | 2 | 2 | 2 | 2 | 2 | 2 | 2 | 2 | 2 | 2 | 2 |
| Stearic Acid | 0.5 | 0.5 | 0.5 | 0.5 | 0.5 | 0.5 | 0.5 | 0.5 | 0.5 | 0.5 | 0.5 |
| 0,0,0',0'-Tetramethyl 0,0'-thiodi-p-phenylene phosphorothioate (Technical) | 93 | 75 | 50 | 35 | 33 | 35 | 80 | 93 | 80 | 75 | 45 |
| % Technical | 47.5 | 40 | 30 | 20 | 20 | 20 | 40 | 47.5 | 40 | 40 | 24.63 |
| % Real | 42.8 | 36 | 27 | 18 | 18 | 18 | 36 | 42.8 | 36 | 36 | 22.2 |
| Di (2-ethylhexyl) Phthalate | — | 5 | 15 | — | 25 | — | — | — | — | 5 | — |
| Octylepoxytallate | — | — | — | 40 | — | — | 15 | — | 15 | — | 35 |
| Emery Plastalein 9750 (Plasticizer) | — | — | — | — | — | 40 | — | — | — | — | — |
| Carbon Black | — | — | — | — | — | — | 0.2 | 0.2 | — | 0.2 | 0.2 |

Table V

Temephos Flea Collar Activity Against *Ctenocephalides felis* on Dogs
Dogs with Complete Control/Dogs Treated

| | Weeks after Treatment | | | | | | | | | | | | | | | | |
|---|---|---|---|---|---|---|---|---|---|---|---|---|---|---|---|---|---|
| Collar No. | 0 | 1 | 2 | 3 | 4 | 5 | 6 | 7 | 9 | 10 | 11 | 17 | 20 | 21 | 22 | 23 | 30 |
| 1 | 4/4 | 4/4 | 4/4 | 4/4 | | 4/4 | | | | 4/4 | | 2/2 | 2/2 | 2/2 | | | 2/2 |

Table V-continued

Temephos Flea Collar Activity Against *Ctenocephalides felis* on Dogs
Dogs with Complete Control/Dogs Treated

| Collar No. | 0 | 1 | 2 | 3 | 4 | 5 | 6 | 7 | 9 | 10 | 11 | 17 | 20 | 21 | 22 | 23 | 30 |
|---|---|---|---|---|---|---|---|---|---|---|---|---|---|---|---|---|---|
| 2 | 3/3 | 3/3 | 3/3 | | 3/3 | | 3/3 | | | | 3/3 | 2/2 | 1/1 | 1/1 | 1/1 | Terminated | |
| 3 | 2/4 | 3/4 | 3/4 | 4/4 | | 3/4 | Terminated | | | | | | | | | | |
| 4 | 1/3 | 3/3 | 3/3 | | 3/3 | | 3/3 | | | | 3/3 | 2/2 | 2/2 | 1/2 | 2/2 | Terminated | |
| 5 | 0/3 | 2/3 | 3/3 | | 1/3 | | 2/3 | Terminated | | | | | | | | | |
| 6 | 0/3 | 2/3 | 1/3 | | 2/3 | | 3/3 | Terminated | | | | | | | | | |
| 7 | 2/3 | 3/3 | 3/3 | | 3/3 | | 2/2 | | | 2/2 | 2/2 | Terminated | | | | | |
| 8 | 3/3 | 3/3 | 3/3 | | 3/3 | | 3/3 | | | | 3/3 | | 3/3 | 2/3* | 2/2 | | |
| 9 | 3/3 | 3/3 | 3/3 | | 3/3 | | 2/2 | | | 2/2 | 2/2 | Terminated | | | | | |
| 10 | 2/3 | 3/3 | 3/3 | | 3/3 | | 3/3 | | | 3/3 | 3/3 | Terminated | | | | | |
| 11 | 3/3 | 3/3 | 3/3 | 3/3 | | 3/3 | | 3/3 | 3/3 | | | | | | | | |
| Untreated Animals | 0/3 | 0/5 | 0/5 | 0/5 | 0/5 | 0/5 | 0/5 | | | 0/5 | 0/5 | 0/5 | 0/5 | 0/5 | 0/5 | | |

*Severe Case of Mange: No Hair Left; Dog Sacrificed

We claim:

1. A method for the prolonged control of siphonaptera on dogs and cats, comprising attaching to the dogs or cats a flexible collar of a composition of a polyvinyl chloride resin having a weight average molecular weight of from 60,000 to 280,000 and an inherent viscosity of from about 0.5 to 1.2, and as the active siphonapteracidal agent from 13% to 50% by weight of 0,0,0′,0′-tetramethyl 0,0′-thiodi-p-phenylene phosphorothioate around the neck of the dog or cat which is to be protected against siphonaptera infestation or reinfestation.

2. A method for the prevention and control of siphonaptera infestation on dogs and cats which comprises attaching to said dogs and cats an extruded flexible collar containing from 45% to 63% of a polyvinyl chloride resin having a weight average molecular weight of from 60,000 to 280,000 and an inherent viscosity of from about 0.5 to 1.2, from 36% to 50% by weight of 0,0,0′,0′-tetramethyl 0,0′-thio-di-p-phenylene phosphorothioate and from 1% to 3% by weight of a resin stabilizing agent.

3. A method for the control of siphonaptera on dogs and cats according to claim 2 with the additional elements of from 0.0% to 2.0% by weight of a lubricant and from 0% to 2% by weight of a pigment.

4. A method for the control of siphonaptera on dogs and cats according to claim 3 wherein the polyvinyl chloride resin has a weight average molecular weight between 80,000 and 230,000 and an inherent viscosity of from 0.67 to 1.07.

5. A method for the control of siphonaptera on dogs and cats according to claim 4 wherein the stabilizing agent is an organo metal stabilizer, the lubricant is a metal stearate, stearic acid, paraffin wax, amide wax or low molecular weight polyethylene and the pigment is carbon black, titanium dioxide, a quinacridone, an anthraquinone, litholrubine or alizarine maroon.

6. A method for the control of siphonaptera on dogs and cats comprising attaching to the dogs and cats a flexible collar of a dry blended siphonapteracidal resin composition comprising from 47.4% of 63.5% by weight of a polyvinyl chloride resin having a weight average molecular weight of from 60,000 to 280,000 and an inherent viscosity of from about 0.5 to 1.2, from 13% to 40% by weight of 0,0,0′,0′-tetramethyl 0,0′-thiodi-p-phenylene phosphorothioate, from 22.5% to 7.6% by weight of a secondary plasticizing agent having a molecular weight of from 400 to 1000 and selected from epoxidized soybean oil, epoxidized linseed oil, epoxidized tall oil ester or epoxidized butyl ester, of linseed oil acids, from 1% to 3% by weight of a heat stabilizing agent for the resin, from 0.0% to 2.0% by weight of a lubricant and from 0.0% to 2.0% by weight of a pigment.

7. A method for the control of siphonaptera on dogs and cats according to claim 6 wherein the polyvinyl chloride amounts to from 47.4% to 58.5% by weight of the composition and has a weight average molecular weight between 80,000 and 230,000 and an inherent viscosity between 0.67 and 1.07 and the phosphorothioate amounts to 18% to 40% by weight of the composition.

8. A method for the control of siphonaptera on dogs and cats according to claim 7 wherein the plasticizing agent is epoxidized soybean oil.

9. A method for the control of siphonaptera on dogs and cats comprising attaching to the dogs and cats a flexible collar of a dry blended siphonapteracidal resin composition comprising from 32% to 40% by weight of 0,0,0′,0′-tetramethyl 0,0′-thiodi-p-phenylene phosphorothioate, from 52.25% to 60.5% by weight of a polyvinyl chloride resin having an inherent viscosity of from about 0.5 to 1.2 and a weight average molecular weight of from 60,000 to 280,000, from 6.5% to 2.75% by weight of dioctyl phthalate, from 1% to 3% by weight of a stabilizing agent for the resin, and from 0.0% to 2.0% by weight of a lubricant.

10. A method for the control of siphonaptera on dogs and cats according to claim 9 wherein the polyvinyl chloride resin has a weight average molecular weight between 80,000 and 230,000 and an inherent viscosity of from 0.67 to 1.07.

11. A method for the control of siphonaptera on dogs and cats according to claim 10 wherein the resin is polyvinyl chloride having an inherent viscosity of about 0.80 and the secondary plasticizing agent is present in about 2.75% by weight of the composition.

* * * * *